US007651989B2

(12) United States Patent
MacDonald et al.

(10) Patent No.: US 7,651,989 B2
(45) **Date of Patent: *Jan. 26, 2010**

(54) SINGLE PHASE COLOR CHANGE AGENTS

(75) Inventors: John Gavin MacDonald, Decatur, GA (US); Yanbin Huang, Roswell, GA (US); Kaiyuan Yang, Cumming, GA (US); Jaeho Kim, Roswell, GA (US); Ning Wei, Roswell, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/651,421

(22) Filed: Aug. 29, 2003

(65) Prior Publication Data

US 2005/0049157 A1 Mar. 3, 2005

(51) Int. Cl.
*A61K 7/00* (2006.01)

(52) U.S. Cl. ........................ 510/130; 510/158; 510/169; 510/481; 510/488; 510/491; 510/508

(58) Field of Classification Search ................. 510/130, 510/156, 424, 481; 436/136
See application file for complete search history.

(56) References Cited

U.S. PATENT DOCUMENTS

| | | | |
|---|---|---|---|
| 2,445,994 | A | 7/1948 | Benson et al. |
| 2,496,270 | A | 2/1950 | Coler |
| 3,042,621 | A | 7/1962 | Kirschenbauer |
| 3,584,115 | A | 6/1971 | Gebhart et al. |
| 3,600,060 | A | 8/1971 | Churchill et al. |
| 3,619,254 | A | 11/1971 | Davis |
| 3,650,831 | A | 3/1972 | Jungermann et al. |
| 3,658,985 | A | 4/1972 | Olson, Jr. et al. |
| 3,669,891 | A | 6/1972 | Greenwood et al. |
| 3,755,064 | A | 8/1973 | Maierson |
| 3,769,398 | A | 10/1973 | Hewitt |
| 3,770,641 | A | 11/1973 | Cantor et al. |
| 3,849,241 | A | 11/1974 | Butin et al. |
| 3,926,830 | A | 12/1975 | Horiguchi et al. |
| 3,935,129 | A | 1/1976 | Jabalee |
| 4,000,317 | A | 12/1976 | Menda et al. |
| 4,013,787 | A | 3/1977 | Varierberghe et al. |
| 4,015,937 | A | 4/1977 | Miyamoto et al. |
| 4,016,089 | A | 4/1977 | Regan et al. |
| 4,022,706 | A | 5/1977 | Davis |
| 4,028,118 | A | 6/1977 | Nakasuji et al. |
| 4,038,148 | A | 7/1977 | Miller et al. |
| 4,070,510 | A | 1/1978 | Kahn |

(Continued)

FOREIGN PATENT DOCUMENTS

| | | |
|---|---|---|
| CA | 1 182 373 | 2/1985 |

(Continued)

OTHER PUBLICATIONS

Abstract, CN 1,086,256, May 4, 1994, Wu et al.

(Continued)

*Primary Examiner*—Necholus Ogden, Jr.
(74) *Attorney, Agent, or Firm*—Dority & Manning, P.A.

(57) ABSTRACT

There is provided a color change composition that remains stable in a single phase and that contains an indicator that produces an observable color change after a period of time to show that sufficient cleaning has been done or to indicate the thoroughness of the cleaning. This use indicating color change is useful for, for example, in soap for teaching children to wash their hands for a sufficient period of time. This composition may be added to many different base materials to indicate time of use or as a way to introduce enjoyment to the activity.

19 Claims, 5 Drawing Sheets

U.S. PATENT DOCUMENTS

| | | | | |
|---|---|---|---|---|
| 4,128,508 | A | 12/1978 | Munden | |
| 4,129,515 | A | 12/1978 | Foster | |
| 4,145,413 | A | 3/1979 | Usdin et al. | |
| 4,150,106 | A | 4/1979 | Assal et al. | |
| 4,154,706 | A | 5/1979 | Kenkare et al. | |
| 4,169,811 | A * | 10/1979 | Yoshikawa et al. | 436/138 |
| 4,174,292 | A * | 11/1979 | Seidenberger et al. | 510/100 |
| 4,193,888 | A | 3/1980 | McHugh | |
| 4,224,195 | A | 9/1980 | Kawasaki et al. | |
| 4,248,597 | A | 2/1981 | McNeely | |
| 4,257,188 | A | 3/1981 | Barker | |
| 4,259,204 | A | 3/1981 | Homma | |
| 4,311,479 | A | 1/1982 | Fenn et al. | |
| 4,313,393 | A | 2/1982 | Barbuscio et al. | |
| 4,329,334 | A | 5/1982 | Su et al. | |
| 4,329,335 | A | 5/1982 | Su et al. | |
| 4,329,336 | A | 5/1982 | Su et al. | |
| 4,349,509 | A * | 9/1982 | Yoshikawa et al. | 422/57 |
| 4,368,147 | A * | 1/1983 | Inamorato et al. | 510/340 |
| 4,381,920 | A | 5/1983 | Garlen | |
| 4,425,161 | A | 1/1984 | Shibahasi et al. | |
| 4,450,091 | A | 5/1984 | Schmolka | |
| 4,472,507 | A | 9/1984 | Pluim, Jr. | |
| 4,499,001 | A | 2/1985 | Eoga | |
| 4,526,701 | A | 7/1985 | Rubin | |
| 4,595,526 | A | 6/1986 | Lai | |
| 4,666,621 | A | 5/1987 | Clark et al. | |
| 4,678,658 | A | 7/1987 | Casey et al. | |
| 4,678,704 | A | 7/1987 | Fellows | |
| 4,690,815 | A | 9/1987 | Deckner | |
| 4,696,258 | A | 9/1987 | Magrath et al. | |
| 4,717,710 | A | 1/1988 | Shimizu et al. | |
| 4,725,462 | A | 2/1988 | Kimura | |
| 4,743,398 | A | 5/1988 | Brown et al. | |
| 4,756,906 | A | 7/1988 | Sweeny | |
| 4,793,988 | A | 12/1988 | Casey et al. | |
| 4,818,491 | A | 4/1989 | Fariss | |
| 4,889,728 | A | 12/1989 | Maeda et al. | |
| 4,896,144 | A | 1/1990 | Bogstad | |
| 4,906,395 | A | 3/1990 | Stoesser et al. | |
| 4,917,814 | A | 4/1990 | MacIntyre et al. | |
| 4,921,636 | A | 5/1990 | Traas | |
| 4,930,506 | A | 6/1990 | Ullrich | |
| 4,954,544 | A | 9/1990 | Chandaria | |
| 4,957,949 | A | 9/1990 | Kamada et al. | |
| 4,960,585 | A | 10/1990 | Tehrani | |
| 4,965,063 | A | 10/1990 | Casey et al. | |
| 5,037,843 | A | 8/1991 | Schoenberg | |
| 5,057,303 | A | 10/1991 | Casey | |
| 5,064,635 | A | 11/1991 | Casey | |
| 5,110,492 | A | 5/1992 | Casey | |
| 5,203,327 | A | 4/1993 | Schoendorfer et al. | |
| 5,213,881 | A | 5/1993 | Timmons et al. | |
| 5,279,735 | A | 1/1994 | Cosentino et al. | |
| 5,320,835 | A | 6/1994 | Pahlck et al. | |
| 5,380,528 | A | 1/1995 | Alban et al. | |
| 5,382,433 | A | 1/1995 | Pahlck et al. | |
| 5,420,118 | A | 5/1995 | Alban et al. | |
| 5,427,708 | A | 6/1995 | Stark | |
| 5,431,697 | A | 7/1995 | Kamata et al. | |
| 5,443,987 | A | 8/1995 | DeCicco et al. | |
| 5,460,647 | A | 10/1995 | Snedeker et al. | |
| 5,460,805 | A | 10/1995 | Davis et al. | |
| 5,466,465 | A | 11/1995 | Royds et al. | |
| 5,478,361 | A | 12/1995 | Sumii et al. | |
| 5,482,654 | A | 1/1996 | Luttrell et al. | |
| 5,486,228 | A | 1/1996 | Miller et al. | |
| 5,503,583 | A | 4/1996 | Hippely et al. | |
| 5,523,075 | A | 6/1996 | Fuerst et al. | |
| 5,554,361 | A | 9/1996 | Dixon | |
| 5,567,420 | A | 10/1996 | McEleney et al. | |
| 5,581,090 | A | 12/1996 | Goudjil | |
| 5,591,255 | A | 1/1997 | Small et al. | |
| 5,595,754 | A | 1/1997 | Ito et al. | |
| 5,597,556 | A | 1/1997 | Moghe et al. | |
| 5,612,222 | A | 3/1997 | Gordon et al. | |
| 5,612,541 | A | 3/1997 | Hoffmann et al. | |
| 5,616,722 | A | 4/1997 | Schoenberg et al. | |
| 5,667,798 | A | 9/1997 | Royds et al. | |
| 5,670,469 | A | 9/1997 | Dingus et al. | |
| 5,680,962 | A | 10/1997 | McEleney et al. | |
| 5,686,088 | A | 11/1997 | Mitra et al. | |
| D388,990 | S | 1/1998 | Brandenburg et al. | |
| 5,714,448 | A | 2/1998 | Choy et al. | |
| 5,736,500 | A | 4/1998 | Farnworth et al. | |
| 5,741,592 | A | 4/1998 | Lewis et al. | |
| 5,744,181 | A | 4/1998 | Sornay et al. | |
| 5,753,210 | A | 5/1998 | McEleney et al. | |
| 5,753,244 | A | 5/1998 | Reynolds et al. | |
| 5,763,332 | A | 6/1998 | Gordon et al. | |
| 5,784,162 | A | 7/1998 | Cabib et al. | |
| 5,791,465 | A | 8/1998 | Niki et al. | |
| 5,792,047 | A | 8/1998 | Coggins | |
| 5,792,384 | A | 8/1998 | Warren | |
| 5,793,292 | A | 8/1998 | Ivey, Jr. | |
| 5,817,615 | A | 10/1998 | Garabedian, Jr. et al. | |
| 5,837,645 | A | 11/1998 | Fuerst et al. | |
| 5,842,905 | A | 12/1998 | Lee et al. | |
| 5,851,981 | A | 12/1998 | Choy et al. | |
| 5,858,340 | A | 1/1999 | Briggs et al. | |
| 5,863,663 | A | 1/1999 | Mackey et al. | |
| 5,876,995 | A | 3/1999 | Bryan | |
| 5,900,067 | A | 5/1999 | Jones | |
| 5,904,735 | A | 5/1999 | Gutierrez et al. | |
| 5,908,707 | A | 6/1999 | Cabell et al. | |
| 5,910,421 | A | 6/1999 | Small, Jr. et al. | |
| 5,911,915 | A | 6/1999 | Fonsny et al. | |
| 5,914,177 | A | 6/1999 | Smith, III et al. | |
| 5,929,004 | A | 7/1999 | Ushijima et al. | |
| 5,929,007 | A | 7/1999 | Feng | |
| 5,939,088 | A | 8/1999 | Ito et al. | |
| 5,939,485 | A | 8/1999 | Bromberg et al. | |
| 5,942,438 | A | 8/1999 | Antonoplos et al. | |
| 5,942,478 | A | 8/1999 | Lopes | |
| 5,952,275 | A | 9/1999 | Feferman et al. | |
| 5,955,062 | A | 9/1999 | McEleney et al. | |
| 5,958,383 | A | 9/1999 | McEleney et al. | |
| 5,971,827 | A | 10/1999 | Lee et al. | |
| 5,979,500 | A | 11/1999 | Jahrling et al. | |
| 5,980,922 | A | 11/1999 | Mackey et al. | |
| 5,997,849 | A | 12/1999 | Small et al. | |
| 5,997,891 | A | 12/1999 | Fuerst et al. | |
| 6,007,797 | A | 12/1999 | Bell et al. | |
| 6,038,331 | A | 3/2000 | Johnson | |
| 6,048,123 | A | 4/2000 | Holt et al. | |
| 6,086,858 | A | 7/2000 | McEleney et al. | |
| 6,113,886 | A | 9/2000 | Bryan | |
| 6,114,290 | A | 9/2000 | Lyle et al. | |
| 6,130,435 | A | 10/2000 | Rocklin | |
| 6,132,681 | A | 10/2000 | Faran et al. | |
| 6,139,821 | A | 10/2000 | Fuerst et al. | |
| 6,146,618 | A | 11/2000 | Bell et al. | |
| 6,149,934 | A | 11/2000 | Krzysik et al. | |
| 6,152,358 | A | 11/2000 | Bryan | |
| 6,180,584 | B1 | 1/2001 | Sawan et al. | |
| 6,188,506 | B1 | 2/2001 | Kaiserman et al. | |
| 6,218,189 | B1 | 4/2001 | Antonoplos et al. | |
| 6,236,317 | B1 | 5/2001 | Cohen et al. | |
| 6,247,995 | B1 | 6/2001 | Bryan | |
| 6,248,593 | B1 | 6/2001 | Esswein et al. | |
| 6,267,976 | B1 | 7/2001 | Barnhart et al. | |
| 6,331,515 | B1 * | 12/2001 | Gambogi et al. | 510/424 |
| 6,340,663 | B1 | 1/2002 | Deleo et al. | |
| 6,361,763 | B1 | 3/2002 | Carroll | |

| | | | | |
|---|---|---|---|---|
| 6,392,546 | B1 | 5/2002 | Smith | |
| 6,419,902 | B1 | 7/2002 | Wright | |
| 6,426,701 | B1 | 7/2002 | Levy et al. | |
| 6,429,177 | B1 | 8/2002 | Williams et al. | |
| 6,436,660 | B1 | 8/2002 | Little, II | |
| 6,446,840 | B2 | 9/2002 | Ophardt et al. | |
| 6,465,791 | B1 | 10/2002 | Ribi et al. | |
| 6,531,118 | B1 | 3/2003 | Gonzalez et al. | |
| 6,533,145 | B2 | 3/2003 | Lewis et al. | |
| 6,537,335 | B1 | 3/2003 | Friars et al. | |
| 6,542,568 | B1 | 4/2003 | Howes, Jr. et al. | |
| 6,552,245 | B1 | 4/2003 | Roessler et al. | |
| 6,612,846 | B1 | 9/2003 | Underhill et al. | |
| 6,703,245 | B2 * | 3/2004 | Sumitani et al. | 436/136 |
| 6,727,818 | B1 | 4/2004 | Wildman et al. | |
| 6,733,766 | B2 * | 5/2004 | Gott et al. | 424/401 |
| 6,806,213 | B2 | 10/2004 | Brooks | |
| 6,814,816 | B2 | 11/2004 | Achar et al. | |
| 6,830,557 | B2 | 12/2004 | Paul | |
| 6,832,916 | B2 | 12/2004 | Collopy | |
| 6,846,785 | B2 | 1/2005 | Patel | |
| 6,882,278 | B2 | 4/2005 | Winings et al. | |
| 6,896,521 | B2 | 5/2005 | Underhill et al. | |
| 6,969,378 | B1 | 11/2005 | Vukos et al. | |
| 7,033,614 | B2 | 4/2006 | Linz et al. | |
| 7,053,029 | B2 | 5/2006 | MacDonald | |
| 2002/0028754 | A1 * | 3/2002 | Johansen et al. | 510/302 |
| 2002/0031486 | A1 | 3/2002 | Lunsmann et al. | |
| 2003/0036328 | A1 | 2/2003 | De Leon et al. | |
| 2003/0044366 | A1 | 3/2003 | Dole et al. | |
| 2003/0191036 | A1 | 10/2003 | MacDonald et al. | |
| 2003/0202952 | A1 * | 10/2003 | Wells et al. | 424/70.13 |
| 2004/0048759 | A1 | 3/2004 | Ribble et al. | |
| 2004/0053803 | A1 * | 3/2004 | Lye et al. | 510/392 |
| 2004/0154947 | A1 | 8/2004 | Duranton | |
| 2005/0049157 | A1 | 3/2005 | MacDonald et al. | |
| 2005/0065048 | A1 | 3/2005 | MacDonald et al. | |
| 2005/0075420 | A1 | 4/2005 | Stovold | |
| 2005/0090414 | A1 | 4/2005 | Rich | |
| 2005/0118237 | A1 | 6/2005 | Krzysik et al. | |
| 2005/0125877 | A1 | 6/2005 | Benjamin et al. | |
| 2005/0134465 | A1 | 6/2005 | Rice et al. | |
| 2005/0148490 | A1 | 7/2005 | Krzysik et al. | |
| 2005/0191326 | A1 | 9/2005 | Melker | |
| 2005/0192191 | A1 | 9/2005 | Kramer et al. | |
| 2005/0239029 | A1 | 10/2005 | Yzermans et al. | |
| 2005/0254551 | A1 | 11/2005 | McClure et al. | |
| 2005/0256758 | A1 | 11/2005 | Sierra et al. | |

FOREIGN PATENT DOCUMENTS

| | | | |
|---|---|---|---|
| CA | 1 196 620 | | 11/1985 |
| EP | 0047101 | A2 | 3/1982 |
| EP | 0202621 | * | 11/1986 |
| EP | 0255978 | A2 | 2/1988 |
| EP | 0 377 500 | A2 | 7/1990 |
| EP | 0418049 | A2 | 3/1991 |
| EP | 0418049 | A2 | 3/1991 |
| EP | 0418049 | A3 | 3/1991 |
| EP | 0327345 | B1 | 10/1993 |
| EP | 0 604 996 | A2 | 7/1994 |
| EP | 0471105 | B1 | 11/1996 |
| EP | 0 750 063 | A1 | 12/1996 |
| EP | 0953283 | A1 | 11/1999 |
| EP | 0850039 | B1 | 7/2001 |
| EP | 1211512 | A2 | 6/2002 |
| FR | 2717184 | | 9/1995 |
| GB | 1313180 | | 4/1973 |
| GB | 1281796 | | 7/1974 |
| GB | 1509450 | | 5/1978 |
| GB | 2050829 | | 1/1981 |
| GB | 2305932 | | 4/1997 |
| JP | 08162132 | | 1/1998 |
| WO | WO 89/05114 | A1 | 6/1989 |
| WO | WO 9111171 | A1 | 8/1991 |
| WO | WO 96/14835 | | 5/1996 |
| WO | WO 9629047 | A1 | 9/1996 |
| WO | 97/09957 | | 3/1997 |
| WO | WO 97/25106 | | 7/1997 |
| WO | WO 97/25404 | | 7/1997 |
| WO | WO 97/40814 | | 11/1997 |
| WO | WO 98/03713 | | 1/1998 |
| WO | WO 98/26040 | | 6/1998 |
| WO | 98/29487 | | 7/1998 |
| WO | WO 98/55569 | A1 | 12/1998 |
| WO | WO 99/60089 | | 11/1999 |
| WO | 00/65911 | | 11/2000 |
| WO | WO 0112149 | A1 | 2/2001 |
| WO | WO 01/38480 | A1 | 5/2001 |
| WO | 01/40792 | | 6/2001 |
| WO | WO 01/52811 | A1 | 7/2001 |
| WO | 02/03949 | | 1/2002 |
| WO | 02/18533 | | 3/2002 |
| WO | 02/35220 | | 5/2002 |
| WO | WO 03083033 | A2 | 10/2003 |
| WO | WO 03083033 | A3 | 10/2003 |
| WO | WO 2004026999 | A2 | 4/2004 |
| WO | WO 2004052307 | A2 | 6/2004 |
| WO | WO 2005123023 | A1 | 12/2005 |
| WO | WO 2006137955 | A1 | 12/2006 |

OTHER PUBLICATIONS

Abstract, DE 2,953,574, Mar. 19, 1981, Schimanski.
Abstract, FR 2,198,991, Apr. 5, 1974.
Abstract, FR 2,717,108, Sep. 15, 1995, Julien et al.
Abstract, FR 2,673,640, Sep. 11, 1992, Mairet.
Abstract, FR 2,805,162, Aug. 24, 2001, Casella.
Abstract, WO 02/24846, Mar. 28, 2002, Dreja.
Abstract, JP 1308499 A, Dec. 13, 1989, Shoichiro et al.
Abstract, JP 2957042 B2, Oct. 4, 1999, Masahito et al.
Abstract, JP 63020382 A, Jan. 28, 1988, Naoki et al.
Abstract, JP 73043642 B, Kobayashi.
Abstract, JP 75018482 B, Jun. 30, 1975, Kobayaski.
Abstract, JP 78000389 B, Jan. 7, 1978, KAO Soap Co. Ltd.
Abstract, JP 81035715 B, Aug. 19, 1981, Lion Dentifrice Co. Ltd.
Abstract, JP 51020905 A, Feb. 19, 1976, Dainichiseika Color & Chem Mfg.
Abstract, JP 61081497 A, Apr. 25, 1986, Higuchi.
Abstract, JP 61252298 A, Nov. 10, 1986, Mitsui Petrochem Ind Co. et al.
Abstract, JP 76016046 B, May 21, 1976, Dainichiseika Color & Chem Mfg.
Abstract, JP 76016048 B, May 21, 1976, Kainichiseika Color & Chem Mfg.
Abstract, JP 76039245 B, Oct. 27, 1976, Kobayashi T.
Abstract, JP 79039007 B, Nov. 26, 1979, Daini Seikosha KK.
Abstract, JP 78035570 B, Sep. 28, 1978, Dainichiseika Color & Chem Mfg.
Abstract, JP 93059958 B, Sep. 1, 1993, Mitsui Petrochem Ind Co. Ltd. et al.
Abstract, JP 93059959 B, Sep. 1, 1993, Mitsui Petrochem Ind Co. Ltd. et al.
Abstract, JP 2002/256291 A, Sep. 11, 2002, Altan KK.
Larson, E.L. et al., Association for Professionals in Infection Control and Epidemiology, Inc., "APIC Guideline for Hand Washing and Hand Antisepsis in Health-Care Settings", Table 1, 1995, pp. 1-7.
Flick, E.W., *Cosmetic and Toiletry Formulations*, ISBN 0-8155-0995-2, 1984, Section XII, pp. 501-512.
Abstract of Chinese Patent No. CN1086256, May 4, 1994.
Abstract of German Patent No. DE2953574, Mar. 19, 1981.
Abstract of French Patent No. FR2673640, Sep. 11, 1992.
Abstract of French Patent No. FR2717108, Sep. 15, 1995.
Abstract of French Patent No. FR2805162, Aug. 24, 2001.
Abstract of Japanese Patent No. JP1308499, Dec. 13, 1989.
Abstract of Japanese Patent No. JP02957042, Sep. 17, 1993.

Abstract of Japanese Patent No. JP48047492, Jan. 7, 1978.
Abstract of Japanese Patent No. JP48070711, Sep. 25, 1973.
Abstract of Japanese Patent No. JP49076903, Jul. 24, 1974.
Abstract of Japanese Patent No. JP49081410, Aug. 6, 1974.
Abstract of Japanese Patent No. JP50103508, Aug. 15, 1975.
Abstract of Japanese Patent No. JP51020905, Feb. 19, 1976.
Abstract of Japanese Patent No. JP51020906, Feb. 19, 1976.
Abstract of Japanese Patent No. JP5239498, Sep. 17, 1993.
Abstract of Japanese Patent No. JP53058506, May 26, 1978.
Abstract of Japanese Patent No. JP61081497, Apr. 25, 1986.
Abstract of Japanese Patent No. JP61252297, Nov. 10, 1986.
Abstract of Japanese Patent No. JP61252298, Nov. 10, 1986.
Abstract of Japanese Patent No. JP61252299, Nov. 10, 1986.
Abstract of Japanese Patent No. JP63020382, Jan. 28, 1988.
Abstract of Japanese Patent No. JP73043642, Jun. 23, 1973.
Abstract of Japanese Patent No. JP75018482, Jun. 30, 1975.
Abstract of Japanese Patent No. JP2002256291, Sep. 11, 2002.
Abstract of the Netherlands Patent No. NL7211429 for FR2198991, Apr. 5, 1974.
Abstract of WO 200224846 A2, Mar. 28, 2002.
Article—*A Serious Look at Changeable Silly Putty*, White et al., Chem. Educator, vol. 5, No. 1, 2000, pp. 2-7.
Article—*Thermochromism in Commercial Products*, White et al., Journal of Chemical Education, vol. 76, No. 9, Sep. 1999, pp. 1201-1205.
U.S. Appl. No. 11/155,353, filed Jun. 17, 2005, MacDonald et al., Color-Changing Composition Comprising a Thermochromic Ingredient.
U.S. Appl. No. 11/303,009, filed Dec. 15, 2005, Stahl et al., Color Changing Cleansing Compositon.
Abstract of Japanese Patent No. JP6212670, Aug. 2, 1994.
"DynaColor™ Data Sheet—Thermochromic Offset Ink (Including Litho, Dry and UV Cure Offset Inks)," CTI—Chromatic Technologies, Incorporated, Jul. 2004, pp. 1-2.
DynaColor™ Data Sheet—Thermochromic Water-Based Flexographic Ink, CTI—Chromatic Technologies, Incorporated, Sep. 2004, pp. 1-3.
"Surfactant Encyclopedia," *Cosmetics & Toiletries*, vol. 104, No. 2, Feb. 1989, pp. 67-111.
Barnett, Gabriel, "Emollient Creams and Lotions," Chapter 2, *Cosmetics—Science and Technology*, Second Edition, vol. 1, John Wiley & Sons, Inc., 1972, pp. 27-104.
Boyce, John M. and Didier Pittet, "Guideline for Hand Hygiene in Health-Care Settings—Recommendations of the Healthcare Infection Control Practices Advisory Committee and the HICPAC/SHEA/APIC/IDSA Hand Hygiene Task Force," *MMWR—Morbidity and Mortality Weekly Report*, vol. 51, No. RR-16, Centers for Disease Control and Prevention, Continuing Education Examination, Oct. 25, 2002, pp. 1-48, CE-1 through CE-4.
Flick, Ernest W., "Soaps," Section XII, *Cosmetic and Toiletry Formulations*, Second Edition, Noyes Publications, Park Ridge, New Jersey, 1989, pp. 707-744.
Lockhead, R.Y., "Natural and Modified Natural Polymers and Thickeners and Their Derivatives," pp. 100-113, and "Synthetic Polymers and Thickeners," pp. 113-129, *Cosmetics & Toiletries*, vol. 103, No. 12, Dec. 1988.
Strianse, S.J., "Hand Creams and Lotions," Chapter 5, *Cosmetics—Science and Technology*, Second Edition, vol. 1, John Wiley & Sons, Inc., 1972, pp. 179-222.
Search Report and Written Opinion for PCT/US2006/030104; Feb. 27, 2007.
US 6,290,977, 09/2001, Friars et al. (withdrawn)

* cited by examiner

SINGLE PHASE COLOR CHANGE AGENTS

BACKGROUND OF THE INVENTION

The present invention concerns toiletries like soap for hand, body and surface use, as well as other cleaning products.

The amount of time needed to clean the skin or a surface has been researched extensively. The Association for Professionals in Infection Control and Epidemiology (APIC) *Guideline for Hand Washing and Hand Antisepsis in Health-Care Settings* (1995) (Table 1), recommends a wash time of 10-15 seconds with soap or detergent for routine hand washing for general purposes. The APIC recommends an antimicrobial soap or detergent or alcohol-based rub wash for 10-15 seconds to remove or destroy transient micro-organisms in for example, nursing and food preparation applications. The APIC further recommends an antimicrobial soap or detergent with brushing for at least 120 seconds for surgical applications. The US Centers for Disease Control and Prevention (CDC) recommends up to 5 minutes of hand cleaning for surgical applications. Clearly, the length of time spend washing the hands can have a great effect on eradication of microbes. Thus there is a need for a cleaning formulation that will enable the user to judge how long he has washed his hands in order to comply with the guidelines.

Proper hand washing habits are important for children also. Children in particular need guidance in determining the appropriate amount of time hand washing should be performed. This guidance is generally given by parents or other caregivers and, while important, is not omni-present. In addition to parental guidance, various other mechanisms have been used to encourage longer hand washing times in children. Soaps have been formulated as foams, for example, to increase the enjoyment children find in hand washing and thus to increase the amount of time children spend in washing. Fragrances have also been used to make the hand washing experience more enjoyable. Dual chamber vessels have been used to produce a color change upon the mixing of the components. It has also been suggested that the reactants in the dual chamber system may alternatively be kept together with one component inactive by some means, such as by microencapsulation, until sufficient physical stimulus results in their effective mixing, or that the components be kept separate yet in one container through the use of a non-miscible mixture of two phases. These methods, though possible, are somewhat impractical and expensive. Far simpler would be a system that produces a color change which does not rely on a physical or phase separation to keep the components unmixed.

There is a need for a color changing toiletry or cleaning product that will provide a time delayed indication that a predetermined cleaning interval has passed after dispensing. There is a further need for a toiletry that is also fun for children to use. There is a further need for the color changing chemistry to be made from components that may be premixed and packaged together for later dispensing from a single chamber vessel.

SUMMARY OF THE INVENTION

In response to the difficulties and problems encountered in the prior art, a new composition has been developed which contains a base material and an indicator or color change agent that provides a change detectable by a user some time after dispensing, and which is stable in a single phase and suitable for storage in a single chamber dispenser. The detectable change may occur in from a finite time to at most about 5 minutes after dispensing, though the change generally does not occur until a second or more after dispensing. The change may occur in at between about 1 second and about 120 seconds, or more desirably between about 5 seconds and about 45 seconds, or still more desirably between about 15 and 35 seconds. The color change may occur in about 10 seconds. This color change composition may be added to toiletries such as soaps, skin lotions, colognes, sunscreens, shampoos, gels, toothpastes, mouthwashes and so forth as well as to other cleaning products like surface cleaners and medical disinfectants.

In another aspect, the invention includes a dispenser having a storage chamber and a dispensing opening in liquid communication therewith, and a cleaning composition within the storage chamber. The cleaning composition is a single phase mixture of a surfactant, a reactant and a dye and the cleaning composition changes color after being dispensed.

This invention also encompasses a hygiene teaching aid and a method of developing a hygiene habit. The hygiene teaching aid has an indicator that provides a change detectable to a user after a period of time after dispensing has passed. The method of developing a hygiene habit includes the steps of dispensing soap and water into a user's hands, rubbing the hands together until a change detectable to the user is detected, and washing the hands with water, where the soap contains an indicator that provides the change after a period of time after dispensing the soap into the hands has passed.

DETAILED DESCRIPTION OF THE INVENTION

Figure 1:
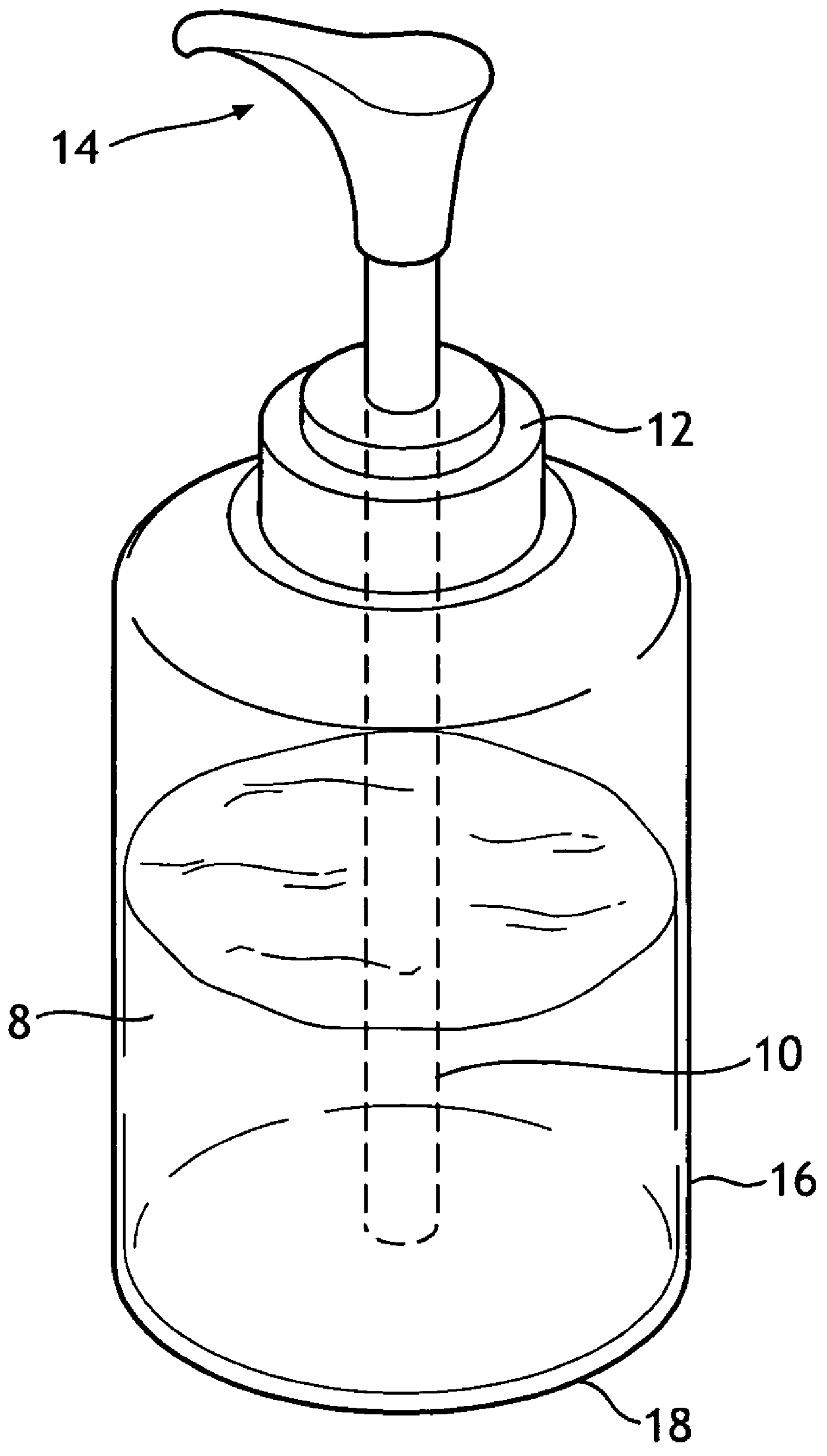
FIG. 1 is a drawing of a pump type liquid soap dispenser.

The invention includes a base or carrier material such as a toiletry or cleaning product, and an indicator that provides a detectable change after a period of time, and that may be stably kept before use in a single closed vessel. It contains at least one dye or pre-dye and a modifying agent that causes a detectable change to occur. The detectable change may be, for example, in color or in shade or degree of color and changes in color may be from colorless to colored, colored to colorless, or from one color to another.

One method of producing the color change effect of this invention is by using color changing electrochemistry based on a reduction/oxidation or redox reaction, in the presence of a dye that is sensitive to this reaction; a redox dye. This reaction involves the transfer of electrons between at least one element or substance and another. In a redox reaction the element that loses electrons increases in valency and so is said to be oxidized and the element gaining electrons is reduced in valency and so is said to be reduced. Conversely, an element that has been oxidized is also referred to as a reducing agent since it must necessarily have reduced another element, i.e., provided one or more electrons to the other element. An element that has been reduced is also referred to as an oxidizing agent since it must necessarily have oxidized another element, i.e., received one or more electrons from the other element. Note that since redox reactions involve the transfer of electrons between at least two elements, it is a requirement that one element must be oxidized and another must be reduced in any redox reaction.

Reduction potential refers to the voltage that a redox reaction is capable of producing or consuming. Much effort has gone into the compilation of reduction potential for various redox reactions and various published sources, such as "Handbook of Photochemistry" by S. Murov, I. Carmichael and G. Hug, published by Marcel Dekker, Inc. N.Y. (1993), ISBN 0-8247-7911-8, are available to those skilled in the art for this information. The invention uses a reducing agent with sufficient redox potential to reduce a dye to a colorless state. Thus in the absence of such a reducing agent the dye, and by extension the base material, would remain the same color before and after use. A successful redox reaction for the practice of the invention should use components having a potential in the range of +0.9 to −0.9 volts. Oxygen, for example, has a redox potential of +0.82 volts.

Oxygen is poorly soluble in water and other materials like, for example, liquid soap formulations. There is normally, therefore, insufficient oxygen in the liquid to oxidize the colorless dye back to the colored state. It is known that the maximum concentration of oxygen in water at room temperature is approximately 13 parts per million (ppm), and, in the practice of the invention, this trace amount is consumed rapidly by the vastly greater amount of reducing agent. As a result, in a stationary, capped bottle, the dye in the liquid formulation will remain in the reduced or colorless state. When a small amount of the liquid formulation is used by placing it on the hands and by hand-washing action, for example in the case of hand soap, it is spread over a large surface area of the skin. This causes the oxygen concentration in this very thin film coating to exceed the concentration that the reducing agent can handle, allowing the dye to be oxidized and the color to develop in the desired indicator time period. Adjusting the concentration of the reducing agent and dye allows the modification of the desired time period from dispensing to color change.

This phenomenon is also observable by vigorously shaking a closed containing having a base material, such as a liquid soap formulation, and the color change indicator of this invention. When this is done, a color is developed due to the increased concentration of oxygen in the liquid soap. This color dissipates slowly after the container is allowed to rest as the oxygen slowly leaves the liquid soap. The reducing agent eventually overcomes the oxygen concentration in the liquid soap and reduces the oxidized dye back to the colorless state.

In one aspect of the invention, therefore, a redox reaction is triggered when the base material containing the color change composition of this invention is mixed with the air. It is the reaction with the oxygen in the air that is the primary reaction that begins the color change. In the case of a liquid hand soap, as discussed above for example, the action of rubbing the hands together results in mixing air into the soap to begin the reaction. In the redox reaction with oxygen, the oxygen is reduced and the dye is oxidized. As shown below (e.g. Example 1), this primary redox reaction results in a direct change in color, such as those reactions using a reducing agent and dye where the dye is a redox dye. When the color change composition is in storage, the redox dye is kept in its unoxidized state by the action of the reducing agent reacting with the available oxygen. Once the composition is in contact with an excess of oxygen such as when it is dispensed, the reducing agent is exhausted through oxidation and the redox dye then takes part in the oxidation, producing the color change.

This aspect of the invention, as discussed above, includes a redox dye and a reducing agent. These components are elaborated upon as follows:

Redox Dyes

Redox dyes include but are not limited to Food Blue 1, 2 and Food Green 3, Basic Blue 17, resazurin, FD&C Blue No. 2, FD&C Green No. 3,1,9-dimethyl methylene blue, and saframine O. Suitable dyes include but are not limited to members of the thiazine, oxazines, azine and indigo dye classes. Other redox dye candidates have been identified allowing the following color changes to occur with this system:

| | |
|---|---|
| Colorless to blue | Basic Blue 17 |
| Colorless to red | Resazurin (low dye concentration) |
| Yellow (similar in color to Dial liquid soap) to green | FD&C Green No. 3 |
| Yellow to purple | 1,9-dimethyl methylene blue |
| Yellow to red | Resazurin (higher dye conc.) |
| Yellow to pink | Saframine O |

Food grade dyes were evaluated as dye candidates in the reducing agent/redox dye color change liquid soap formulation and a variety of color changing chemistries are available. The results of this evaluation may be seen in Example 6.

The amount of dye used in the practice of the invention is desirably between about 0.001 and 0.5 weight percent, more desirably between about 0.002 and 0.25 weight percent dye and still more desirably between about 0.003 and 0.1 weight percent.

Reducing Agents

Reducing agents include but are not limited to any compound that is compatible with the redox dye and base material being used and which will react with oxygen in a redox reaction. Upon mixing the base material, dye and reducing agent, the reducing agent reduces the dye to the colorless "reduced dye". The base material will generally have a small amount of dissolved oxygen already present, and this oxygen reacts (oxidizes) with the "reduced dye" to form the colored dye. This is quickly re-converted back to the reduced form (colorless) by the high concentration of the reducing agent present in the formulation. The oxygen is therefore consumed in the formulation and converted, eventually, to water. The formulation therefore has essentially no oxygen present in it. This equilibrium may be represented as follows:

$$\text{DYE (Color)} \underset{\text{Oxygen}}{\overset{\text{Reducing Agent}}{\rightleftharpoons}} \text{Reduced DYE (Colorless)}$$

Thin film, high oxygen exposure — Closed bottle, low/no oxygen

In the case of a liquid soap formulation, for example, on dispensing the soap onto the hand(s) and conducting hand-washing action, the soap is spread out over the hands as a thin layer and diluted with water. This action allows atmospheric oxygen to penetrate this thin layer and oxidize the dye to the colored state. The reducing agent reduces this dye to an extent but is eventually overwhelmed by the excess amount of atmospheric oxygen introduced by virtue of the large exposed surface area, and is consumed, allowing the dye to remain colored. This color formation gives the visual indication that sufficient hand-washing time has occurred. The "battle" of oxygen against reducing agent for the dye takes a finite time, thus allowing control of the hand-washing period for indicating purposes.

When a liquid soap formulation containing the inventive composition in a container is shaken, oxygen is introduced into the soap. The oxygen converts the colorless "reduced dye" to the colored form, but due to the solubility of oxygen in water being only about 13 parts per million (ppm) the oxygen is rapidly consumed in converting some of the dye. This colored oxidized dye is reduced by the larger concentration of reducing agent and the soap quickly becomes colorless once more. With repeated vigorous shake-cycles it may be possible to consume the reducing agent entirely, in which case the soap would remain colored.

Reducing agents suitable for producing a redox reaction upon exposure to the oxygen in air include but are not limited to sugars like glucose, galactose and xylose and so forth. Other suitable reducing agents include but are not limited to hydroquinone, ascorbic acid, cysteine, dithionite, ferric ion, copper ion, silver ion, chlorine, phenols, permanganate ion, glucothione, iodine and mixtures thereof. Metal complexes that can function as reducing agents are also suitable for the practice of this invention. Metal complexes include but are not limited to mononuclear, binuclear and cluster complexes like iron protoporyphyrin complexes and iron-sulfur proteins.

The reaction rates are different for the same amount by weight of different reducing agents and this may be an additional method of modifying the color change to the desired time period. Various sugars were evaluated as reducing agents and the results of this evaluation may be seen in Example 6.

The amount of reducing agent used in the practice of this invention is desirably between about 0.1 and 2.0 weight percent, more desirably between about 0.2 and 1.50 weight percent and still more desirably between about 0.3 and 1 weight percent. It is also desirable that the ratio of reducing agent to redox dye be at least about 2 to 1, more desirably at least about 5 to 1 and still more desirably at least about 10 to 1.

In another aspect of the invention, the primary redox reaction begun with contact with air may then initiate a secondary reaction that results in a color change. An example of this aspect is shown in Example 2. The primary reaction between a reducing agent and the air may, for example, result in a change in pH of the solution. The change in pH may then cause a color change through the use of pH sensitive dyes like those described in, for example *The Sigma-Aldrich Handbook of Stains, Dyes and Indicators* by the Aldrich Chemical Company (1990), ISBN 0-941633-22-5, at the inside back cover. Catalysts and buffers may also be used to control the reaction kinetics. The components of this aspect of the invention are discussed immediately below.

PH Sensitive Dyes

Suitable dyes may be activated between about the pHs of 4 and 9 or more particularly 5 and 8 for normal use on the human body and may thus be paired with the primary redox reactants in such a way as to produce the most effective color change. Suitable pH sensitive dyes include but are not limited to carminic acid, bromocresol green, chrysoidin, methyl red/Na salt, alizarin red S, cochineal, chlorphenol red, bromocresol purple, 4-nitrophenol, alizarin, nitrazine yellow, bromothymol blue, brilliant yellow, neutral red, rosolic acid, phenol red, 3-nitrophenol, orange II and so forth.

The amount of dye used in the practice of the invention should be between about 0.001 and 0.5 weight percent, more desirably between about 0.002 and 0.25 weight percent dye and still more desirably between about 0.003 and 0.1 weight percent.

Catalysts

The use of a catalyst, as the term is commonly understood in the scientific community, increases the ability of the designer to control the speed of the reaction by selecting the type and amount of catalyst present. An example of a catalyst is an enzyme, e.g.; glucose oxidase. The catalyst produces a change in the pH of the solution upon reaction with air (oxygen), which subsequently produces a color change through the use of a pH sensitive dye. An example of the effect of catalysts on the reaction is shown in Example 2. If a catalyst is used it may be present in an amount between about 0.001 and 0.5 weight percent.

pH Buffering pH buffering is commonly used in chemical reactions to control the rate of reaction. In the case of the invention, a pH buffer may be used for this purpose as well as to increase the stability of the mixture in storage and transportation. The buffering capacity may be designed to be sufficient for any pH change induced by the relatively small amount of oxygen contained within the solution or in the "headspace" above the solution in the storage container, yet below that needed for buffering of the solution when exposed to large amounts of oxygen as occurs during use. Suitable pH buffers include but are not limited to sodium laureth sulfate and citric acid, and so forth. Selection of one or more buffering agents, however, would be dependent upon the reactants used, the choice of dye and the catalyst used, if any, and are within the ability of those skilled in the art to select.

In yet another aspect of the invention, the color change caused by both the redox dye and the pH sensitive dye compositions may be used together in the same solution. More than one reducing agent may also be employed to initiate the color change-producing redox reaction with the oxygen in the air.

The amount of time between dispensing and color change will depend on the formulation used as well as the energy used to introduce oxygen to the solution. Dispensing a color change soap solution onto the hands, followed by vigorous hand rubbing, for example, will result in a more rapid color change than would less vigorous hand rubbing. Reducing the amounts of dye and other components will likewise result in lengthening the time to the color change. Relatively simple experimentation with the amounts and types of soap, dye and other components discussed herein allows one to design a color change composition that will change color in a length of time up to about 5 minutes.

It is believed that the reversible color change feature of the invention would provide a fun and play aspect to a single chamber liquid soap. Each change of color from its starting color to a second color and back to the starting color is a "cycle" and it should also be noted that the color change cycle is dependent on the dye concentration. In the laboratory experiments discussed herein, the number of color change cycles possible ranged from 12 cycles to 35 cycles, depending on the dye concentration.

Dispensers

The indicator composition of the invention may be dispensed with, for example, liquid soap, in a number of different ways. One particular example is by the use of the liquid pump type dispenser, as illustrated in FIG. 1. This dispenser contains soap 8, has a lower intake member 10, a central pump assembly 12 and an outlet member 14. The lower intake member 10 extends downward into a supply container 16 for liquid soap 8 storage to a point near the bottom 18. The lower intake member 10 within the supply container 16 is shown in dashed lines. The central pump assembly 12 has a check-valve and spring arrangement (not shown) which allows the one-way movement of liquid soap 8 through the pump assembly 12. When a user pushes down on the upper outlet member 14, the pump assembly 12 is actuated, moving liquid soap 8 upwardly from the supply container 16, through the intake member 10 and pump assembly 12 and discharging it from the outlet member 14.

Figure 2:
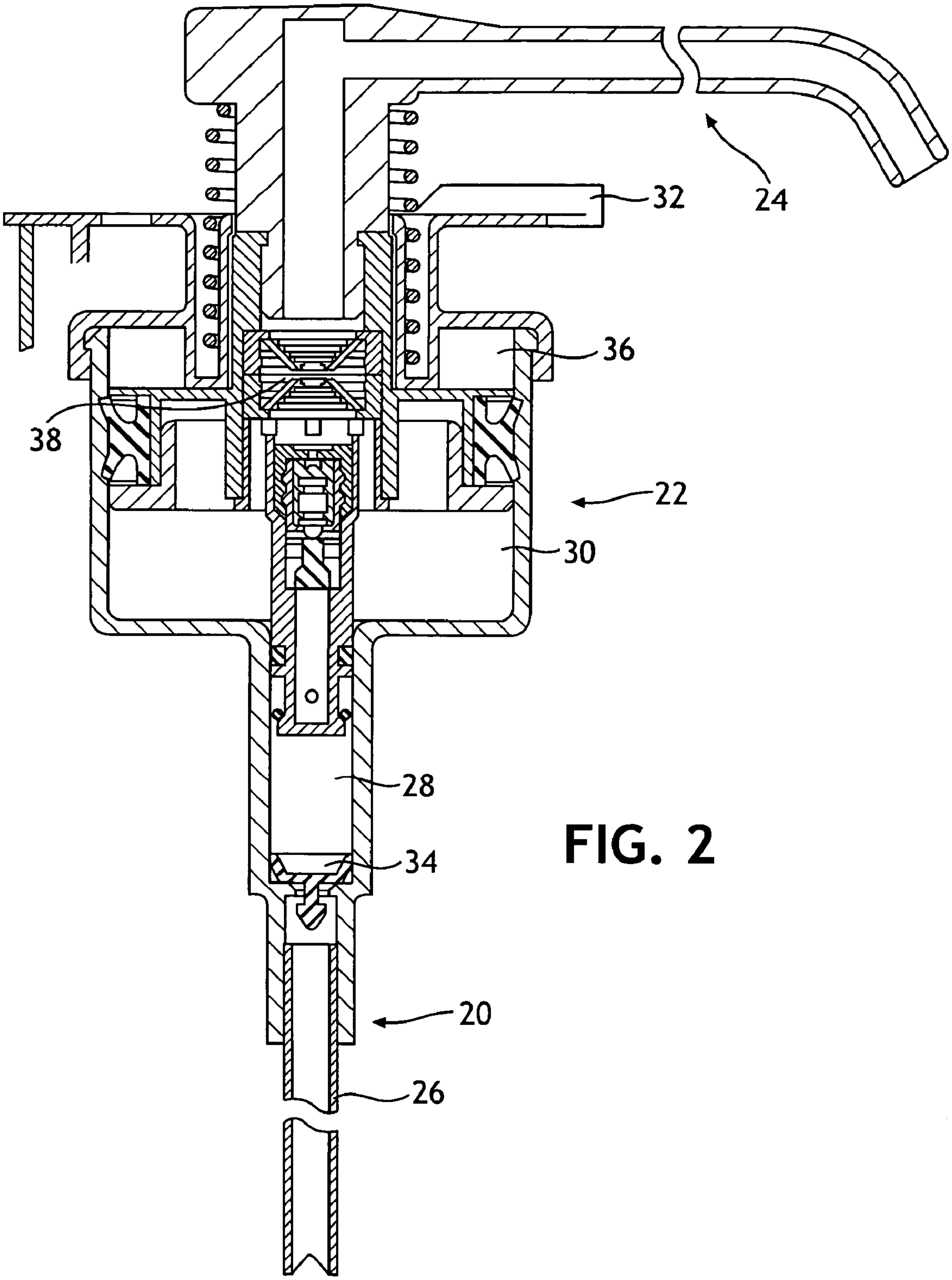
FIG. 2 is a drawing of a foaming liquid soap dispenser using a pump.

It is believed that any of numerous dispensing mechanisms can be used with the present invention. As a further example is a foaming pump dispenser, such as, for example, described in U.S. Pat. No. 6,446,840. In reference to FIG. 2, a foaming dispenser has a lower intake member 20, a central pump assembly 22, and an upper outlet member 24. The intake member 20 has an open intake tube 26 extending into the liquid soap during normal operation, and connected to a lower extension 28 forming a liquid chamber 30 projecting from a housing 32. A check-valve 34 permits flow only up into the chamber 30 from the tube 26. The central pump assembly 22 has a foam-generating nozzle which, when pressurized with a liquid on one sides emits on the opposite side a swirling aerosol spray. Axial passages and radial ports allow air flow from the chamber 36 into the chamber 38. The foaming chamber 38 holds a foam generator. The housing 32 is designed to sit on the rim of a supply container holding a body of liquid foamable soap or detergent.

Figure 3:
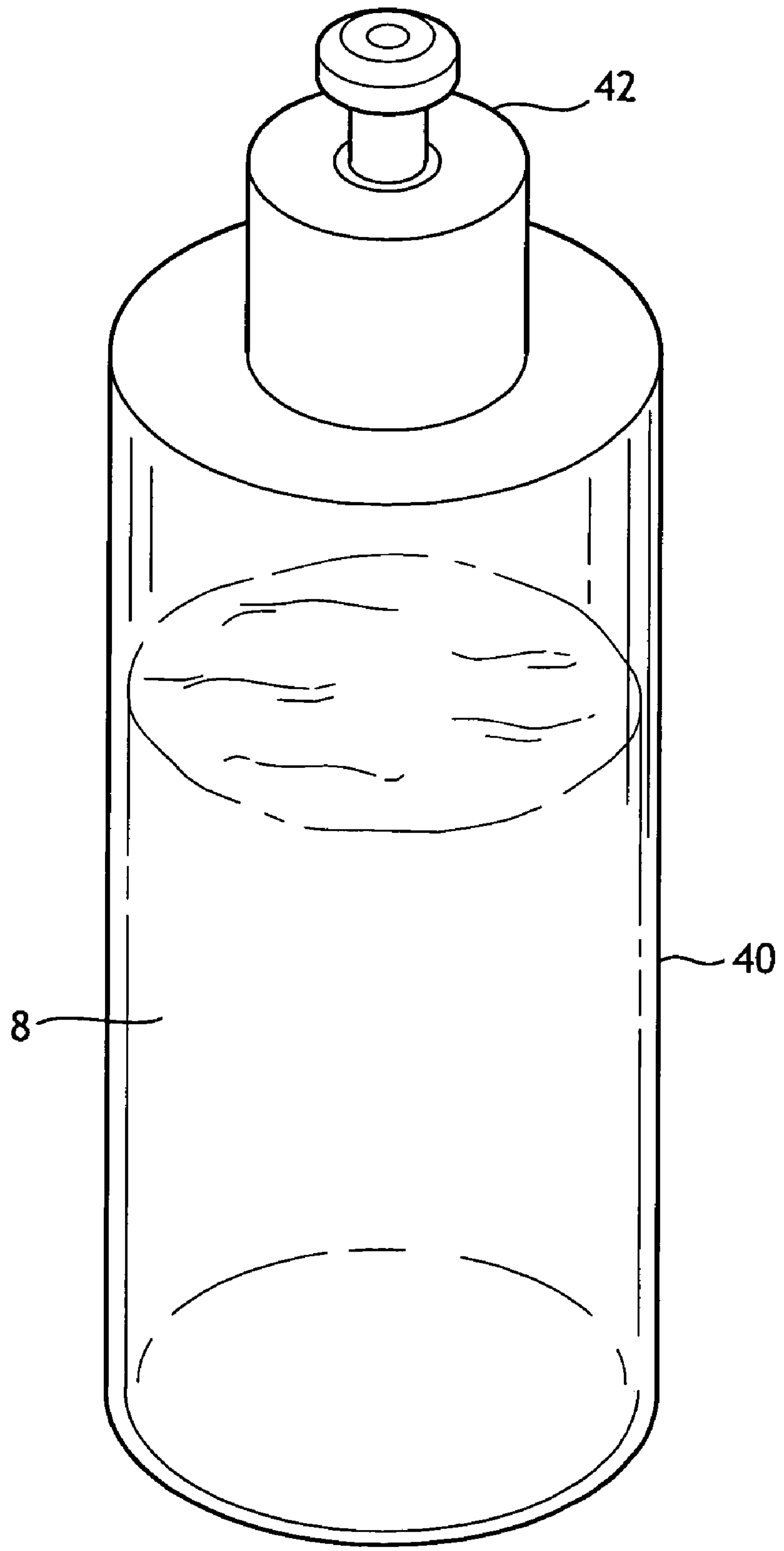
FIG. 3 is a drawing of a pliable storage bottle for liquid soap which may be inverted for soap dispensing.

Still another dispenser is seen in FIG. 3. In this dispenser, the supply container 40 is pliable and is fitted with a valve 42. Withdrawal of liquid soap 8 is accomplished by opening the valve 42, inventing the dispenser, and squeezing the supply container 40 to force soap through the valve 42 and onto, for example, the hands.

Figure 4:
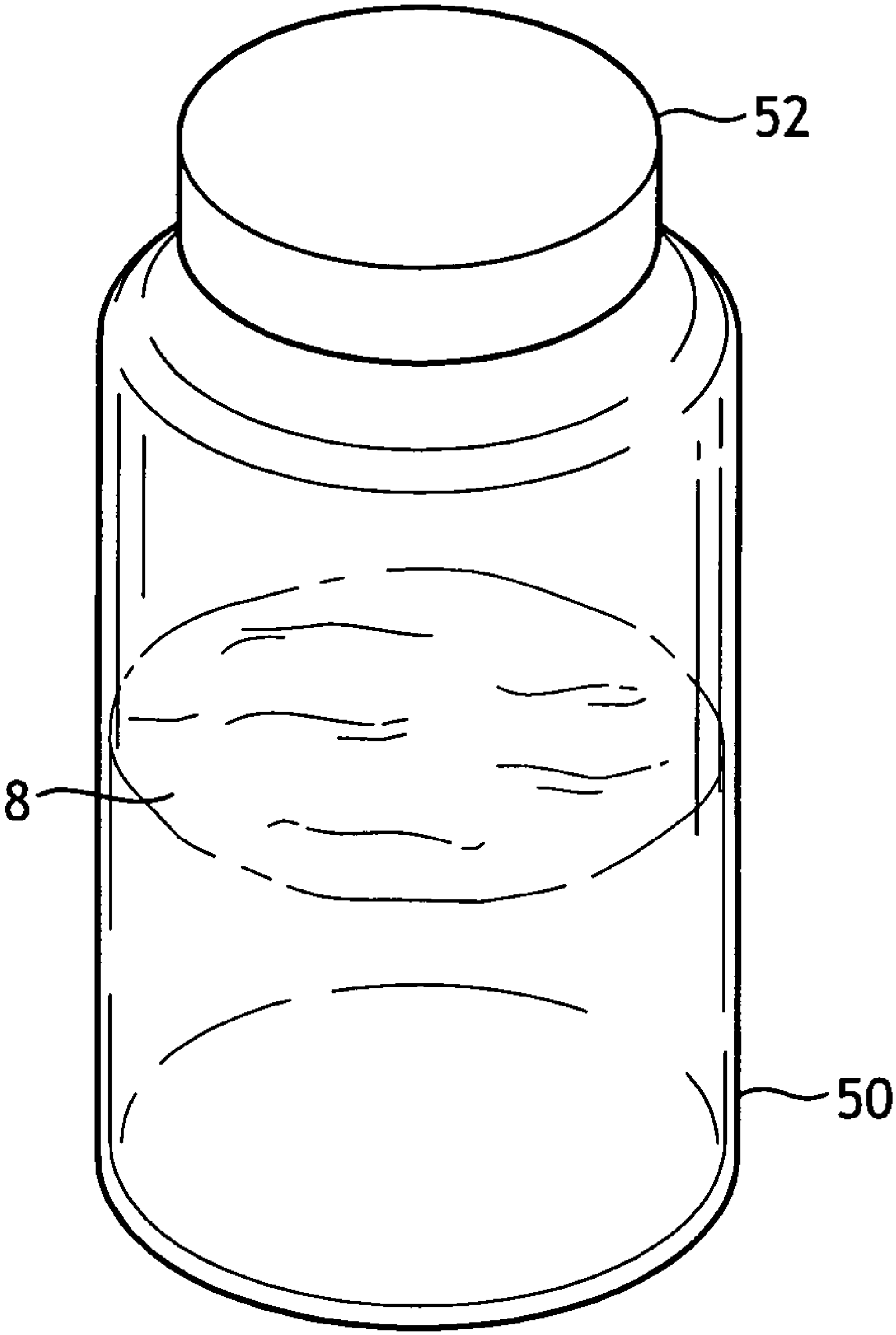
FIG. 4 is a drawing of a non-pliable, manually openable storage container for liquid soap.

Still another dispenser is shown in FIG. 4 and in which the supply container 50 is non-pliable. The supply container 50 is fitted with a removable top 52 which may be unscrewed from the supply container 50 so that liquid soap 8 may be removed manually by a user.

Figure 5:
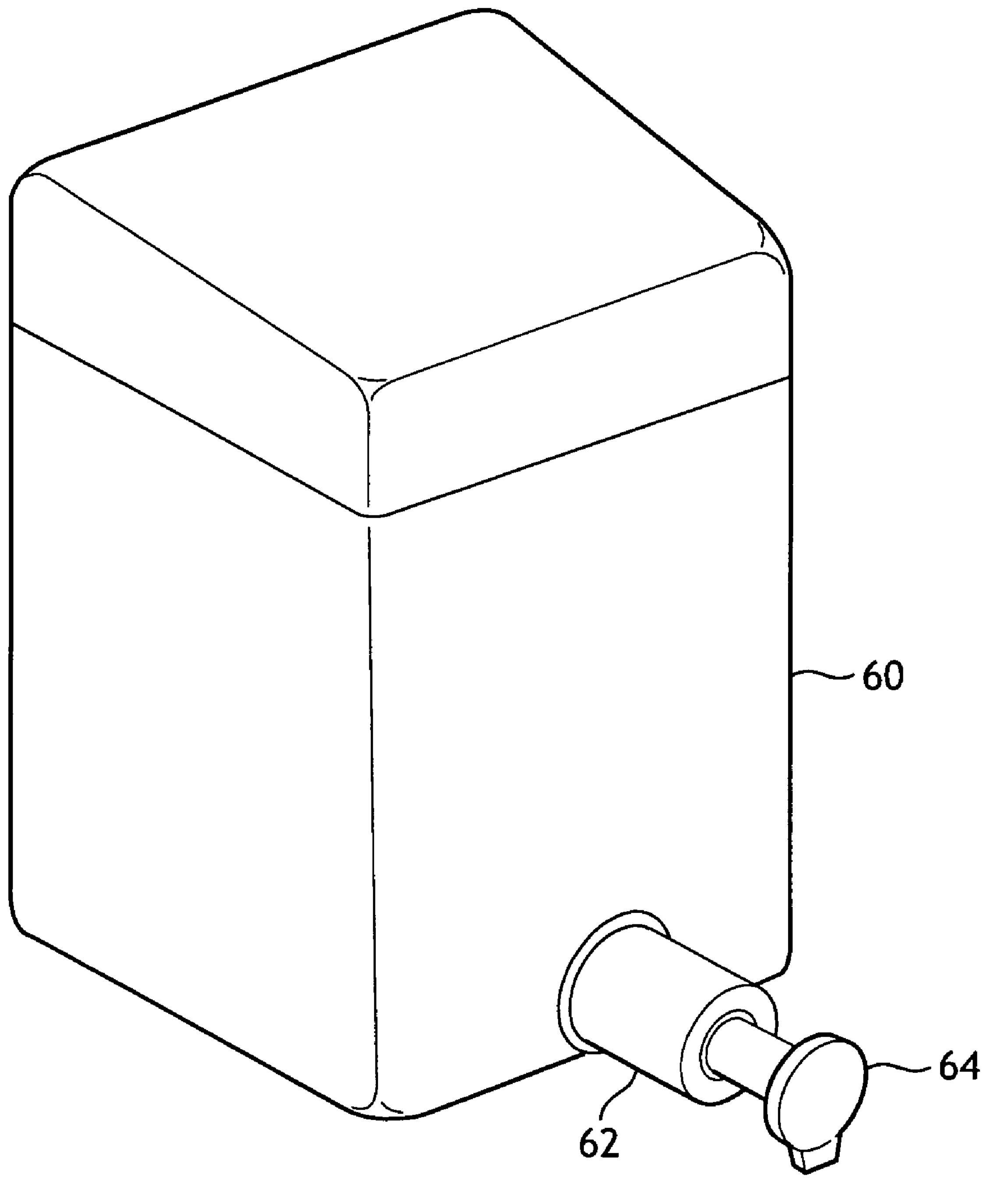
FIG. 5 is a drawing of a pump type liquid soap dispenser suitable for wall mounting.

Yet another example of a dispenser is commonly used in wall mounting installations. This dispenser is depicted in FIG. 5 and described in U.S. Pat. No. 6,533,145 and U.S. Design Pat. No. 388,990, the contents of which are hereby incorporated by reference as if set forth in their entirety, and has a supply container 60, a central pump assembly 62 and an outlet part 64. Similarly to the pump dispenser of FIG. 1, the central pump assembly 62 has a check-valve and spring arrangement (not shown) which allows the one-way movement of liquid soap through the pump assembly 62. When a user pushes on the outlet part 64, the pump assembly 62 is actuated, moving liquid the supply container 60, through the pump assembly 62 and discharging it from the outlet part 64. In various aspects of the inventions, the outlet part 64 may be located below the supply container 60 and the pump assembly 62 may be recessed within the supply container 60.

Base Materials

The color change composition of the invention is suitable for addition to base materials such as toiletries. Toiletries include but are not limited to soaps (liquid and bar), skin lotions, colognes, sunscreens, shampoos, gels, toothpastes, mouthwashes and the like.

Base materials further include but are not limited to cleaning products such as hard surface cleansers and medical disinfectants. Hard surface cleansers incorporating the color change chemistry of the invention may be used in the home or business environment in, for example, food preparation areas. In such uses, the time from application to color change may be adjusted to provide effective microbial elimination. Likewise, medical disinfectants using the color change indicator of this invention can let a user know when a time sufficient for effective microbial control has elapsed.

Many toiletries and cleaners contain similar core ingredients; such as water and surfactants. They may also contain oils, detergents, emulsifiers, film formers, waxes, perfumes, preservatives, emollients, solvents, thickeners, humectants, chelating agents, stabilizers, pH adjusters, and so forth. In U.S. Pat. No. 3,658,985, for example, an anionic based composition contains a minor amount of a fatty acid alkanolamide. U.S. Pat. No. 3,769,398 discloses a betaine-based composition containing minor amounts of nonionic surfactants. U.S. Pat. No. 4,329,335 also discloses a composition containing a betaine surfactant as the major ingredient and minor amounts of a nonionic surfactant and of a fatty acid mono- or di-ethanolamide. U.S. Pat. No. 4,259,204 discloses a composition comprising 0.8 to 20% by weight of an anionic phosphoric acid ester and one additional surfactant which may be either anionic, amphitricha, or nonionic. U.S. Pat. No. 4,329,334 discloses an anionic amphoteric based composition containing a major amount of anionic surfactant and lesser amounts of a betaine and nonionic surfactants.

U.S. Pat. No. 3,935,129 discloses a liquid cleaning composition containing an alkali metal silicate, urea, glycerin, triethanolamine, an anionic detergent and a nonionic detergent. The silicate content determines the amount of anionic and/or nonionic detergent in the liquid cleaning composition. U.S. Pat. No. 4,129,515 discloses a liquid detergent comprising a mixture of substantially equal amounts of anionic and nonionic surfactants, alkanolamines and magnesium salts, and, optionally, zwitterionic surfactants as suds modifiers. U.S. Pat. No. 4,224,195 discloses an aqueous detergent composition comprising a specific group of nonionic detergents, namely, an ethylene oxide of a secondary alcohol, a specific group of anionic detergents, namely, a sulfuric ester salt of an ethylene oxide adduct of a secondary alcohol, and an amphoteric surfactant which may be a betaine, wherein either the anionic or nonionic surfactant may be the major ingredient. Detergent compositions containing all nonionic surfactants are shown in U.S. Pat. Nos. 4,154,706 and 4,329,336. U.S. Pat. No. 4,013,787 discloses a piperazine based polymer in conditioning and shampoo compositions. U.S. Pat. No. 4,450,091 discloses high viscosity compositions containing a blend of an amphoteric betaine surfactant, a polyoxybutylenepolyoxyethylene nonionic detergent, an anionic surfactant, a fatty acid alkanolamide and a polyoxyalkylene glycol fatty ester. U.S. Pat. No. 4,595,526 describes a composition comprising a nonionic surfactant, a betaine surfactant, an anionic surfactant and a C12-C14 fatty acid mono-ethanolamide foam stabilizer. The contents of the patents discussed herein are hereby incorporated by reference as if set forth in their entirety.

Further information on these ingredients may be obtained, for example, by reference to: *Cosmetics & Toiletries*, Vol. 102, No. 3, Mar. 1987; Balsam, M. S., et al., editors, *Cosmetics Science and Technology*, 2nd edition, Vol. 1, pp 27-104 and 179-222 Wiley-Interscience, New York, 1972, Vol. 104, pp 67-111, Feb. 1989; *Cosmetics & Toiletries*, Vol. 103, No. 12, pp 100-129, Dec. 1988, Nikitakis, J. M., editor, *CTFA Cosmetic Ingredient Handbook*, first edition, published by The Cosmetic, Toiletry and Fragrance Association, Inc., Washington, D.C., 1988, Mukhtar, H, editor, *Pharmacology of the Skin*, CRC Press 1992; and Green, F J, *The Sigma-Aldrich Handbook of Stains. Dyes and Indicators*; Aldrich Chemical Company, Milwaukee Wis., 1991, the contents of which are hereby incorporated by reference as if set forth in their entirety.

Exemplary materials that may be used in the practice of this invention further include but are not limited to those discussed in *Cosmetic and Toiletry Formulations* by Ernest W. Flick, ISBN 0-8155-1218-X, second edition, section XII (pages 707-744).

These include but are not limited to for example, the following formulations:

| | wt % |
|---|---|
| Liquid hand soap | |
| EMERY 5310 coconut sulfosuccinate | 20 |
| EMERSAL 6400 sodium lauryl sulfate | 10 |
| EMID 6513 lauramide DEA | 3 |
| EMID 6540 linoleamide DEA | 2 |
| ETHOXYOL 1707 emulsifying acetate ester | 1 |
| EMERSOL 233 oleic acid | 1 |
| EMERESSENCE 1160 rose ether phenoxyethanol | 1 |
| Triethanolamine | 0.5 |
| Deionized water | balance |
| Liquid soap | |
| Ammonium laureth sulfate, 60% | 24 |
| Cocamidopropyl betaine | 6 |
| Stearamidopropyl dimethylamine | 1.5 |
| Sodium chloride | 1.3 |
| Glycol distearate | 1 |
| Citric acid | 0.25 |
| Methylparaben | 0.15 |
| Propylparaben | 0.05 |
| Bronopol | 0.05 |
| Water | balance |
| Bar soap | |
| Soap base 80/20 | 95.68 |
| Water | 1 |
| Antioxidant | 0.07 |
| Perfume oil | 0.75 |
| Titanium dioxide | 0.5 |
| GLUCAM E-20 | 2 |

EXAMPLES

Example 1A

Redox Dye/Reducing Agent Producing Color Change

The formulation used was: 200 grams of Kimberly-Clark Professional antibacterial Clear Skin Cleanser (PCSC C2001-1824), 0.01 gram of Food Blue No. 2 dye and 1.2 grams of glucose sugar. In weight percentage this was 0.005 weight percent dye and 0.6 weight percent sugar and the balance soap. The mixture was stirred at ambient temperature for 20 minutes to dissolve additives and then poured into a dispenser container. On standing, the color turned a pale yellow color.

In this example, Indigo Carmine (Food Blue No. 2, FD&C No. 1) dye, normally blue/green in color, when mixed into a glucose/liquid soap solution, was reduced by the glucose to a pale yellow color. On exposure of the soap mixture to the air and with rubbing on the hands, oxygen oxidized the dye back to the green/blue color in about 10 to 20 seconds. Interestingly, there is not enough oxygen in the soap while sealed in a container to oxidize the reduced dye, thereby allowing it to remain yellow in the container.

As a variation of this Example 1A, a number of additional Examples 1B-1G were conducted with the same ingredients in different proportions and the time to initial color change noted. These examples used a soap solution of 500 ml of Kimberly-Clark Professional antibacterial Clear Skin Cleanser with 9 grams of glucose and a dye solution of 0.2 grams of Food Blue No. 2 in 100 ml of water. Samples were prepared by placing the dye solution in the amounts below into 100 ml beakers and adding the soap solution to make a total volume of 20 ml. Example 1G used 10 ml of the soap and glucose solution with another 9 ml of only soap, with 1 ml of dye solution.

| Glucose Stock Solution (ml) (gram of glucose) | Dye Stock Solution (ml) (mg of dye) | time | Example |
|---|---|---|---|
| 17 (0.170 g) | 3 (6 mg) | <5 sec | 1B |
| 18 (0.180 g) | 2 (4 mg) | 5-10 sec | 1C |
| 19 (0.190 g) | 1 (2 mg) | 15-20 sec | 1D |
| 19.5 (0.195 g) | 0.5 (1 mg) | 40-50 sec | 1E |
| 19.75 (0.198 g) | 0.25 (0.5 mg) | 2 min +/− 10 sec | 1F |
| 10 plus 9 ml soap (0.10 g) | 1 (2 mg) | 15-20 sec | 1G |

Tailoring the time for initial color change can be seen therefore to be a relatively straight forward matter within the range of normal experimentation.

Example 2 pH Change Producing Color Change

The formulation used was: 76 grams of Kimberly-Clark Professional antibacterial Clear Skin Cleanser (PCSC C2001-1824), 1 gram of glucose oxidase enzyme catalyst and a trace amount of chlorophenol red (the initial mixture), followed by the addition of 6.4 milligrams of glucose sugar to 4.7 grams of the initial mixture. The initial mixture remained red upon mixing and after the addition of the glucose (the final mixture). The final mixture was placed on a tile and spread manually, resulting in a gradual color change to yellow in about 20 seconds.

This example of pH change producing a color change is the addition of a glucose enzyme catalyst and chlorophenol red to a soap solution. After mixing, glucose, having a redox potential of −0.42v, was added and the color (red) did not change. Upon agitation in air on a surface, however, sufficient oxygen was introduced to react the glucose, in the presence of the catalyst, to gluconic acid and so reduce the pH of the solution below 6, inducing a color change caused by the chlorophenol red.

Example 3

Redox Dye/Reducing Agent Producing Color Change Using Cysteine/Ascorbic Acid Reagent stock solutions were made having the following compositions:

2.0 grams of Indigo Carmine (Food Blue 1, FD&C Blue 2) redox dye dissolved in 1000 ml of tap water. Indigc Carmine dye is available from the Aldrich Chemical Company of Milwaukee Wis., catalog number 13,116-4.

10 weight percent L-ascorbic acid reducing agent in tap water. Ascorbic acid is available from the Aldrich Chemical Company, catalog number 25,556-4.

10 weight percent DL-cysteine reducing agent in tap water. Cysteine is available from the Aldrich Chemical Company, catalog number 86,167-7.

A series of water solutions were made with 1 ml of Indigo Carmine dye reagent stock solution and made up to 100 ml with tap water. Various amounts of the other two reagent stock solutions were added to this dye solution as shown below. After being shaken to initiate the color change, the compositions were then allowed to equilibrate and were timed for the reverse color change (to colorless) and tested for pH as indicated.

| REAGENT | Volume (ml) of Reagent Stock Solution Added | | | | | | | | | | | |
|---|---|---|---|---|---|---|---|---|---|---|---|---|
| Cysteine | 0 | 0 | 0 | 0 | 1 | 5 | 10 | 20 | 1 | 5 | 10 | 20 |
| Ascorbic Acid | 1 | 5 | 10 | 20 | 0 | 0 | 0 | 0 | 1 | 5 | 10 | 20 |
| Time To Colorless (min) | NC | NC | NC | NC | 90 | 130 | 260 | ? | 260 | 45 | 25 | 10 |
| pH | 6.4 | 6.4 | 6.1 | 6.0 | 6.4 | 6.2 | 6.1 | 5.9 | 6.4 | 6.3 | 6.2 | 6.0 |

NC = No change in color after 19 hours.
? = Turned colorless sometime after 3 hours and before 19 hours.

The cysteine/ascorbic acid solution was tested in liquid soap formulations (PCSC C2001-1824) as well. The water solutions of the reagent stock solutions were added directly to 50 mls of liquid soap in the amounts indicated below. The compositions were again shaken and then allowed to equilibrate and the time to reverse the change color and the pH tested as reported.

| SAMPLE | Volume (ml) of Reagent Stock Solution Added | | | | |
|---|---|---|---|---|---|
| Dye | 1 | 3 | 1 | 1 | 3 |
| Ascorbic Acid | 0 | 0 | 9 | 20 | 20 |
| Cysteine | 0 | 0 | 9 | 20 | 20 |
| Time to colorless (min) | NC | NC | 120 | 60 | 90 |
| pH | 6.7 | 6.7 | 6.1 | 6.0 | 6.0 |

The blue to colorless change is reversible by shaking the liquid to introduce oxygen, which oxidizes the dye back to the blue color in about 20 seconds.

As can be seen from these results, the cysteine/ascorbic acid system can be used to formulate a color changing liquid soap with Indigo Carmine dye. Cysteine alone also causes a reversible de-colorization reaction to occur, but the reaction rate is much slower. In addition, substitutes known to those skilled in the art may be used for these reagents. Cysteine, for example, may substituted with glutathione, though the color change is somewhat slower. Indigo carmine dye may be substituted with 1, 9 dimethyl methylene blue (thiazine dye class) and brilliant cresyl blue acid (thazine dye class).

Example 4

Redox Dye/Reducing Agent Producing Color Change

The formulation used was: 200 grams of Kimberly-Clark Professional Moisturizing Instant Hand Antiseptic as given above, 0.01 gram of Food Blue No. 2 dye and 1.2 grams of glucose sugar. On handwashing, the color turned from colorless to blue in about 10 to 20 seconds.

Example 5

Redox Dye/Reducing Agent Producing Color Change

The formulation used was: 200 grams of Kimberly-Clark Professional Eurobath Foaming Soap (P8273-PS117-81.102), 0.01 gram of Food Blue No. 2 dye and 1.2 grams of glucose sugar. After mixing the ingredients, the white foam was place on the hand and with handwashing action the soap changed from white to blue. The foaming dispenser, as discussed above, also introduced enough oxygen to the soap upon dispensing that the soap changes color even without agitation in approximately 10 to 20 seconds.

Example 6

Redox Dyes Producing Color Change

The dyes were evaluated by preparing the formulation in Example 1A using the corresponding dye, washing the hands with running water, and grading the color and time to change. The following results were obtained.

| Food Dye | Color in Soap | Color on Use | Evaluation |
|---|---|---|---|
| Blue 1 | Yellow | Blue | Works |
| Blue 2 | Yellow | Blue | Works |
| Red 40 | Yellow | Yellow | Fails |
| Green 3 | Yellow | Green | Works |
| Yellow 5 | Yellow | Yellow | Fails |

The study showed that Food Blue 1, 2 and Food Green 3 all work well in the liquid soap formulation.

Example 7

Evaluation Of Simple Sugars

A side-by-side study was carried out to examine the effect of substituting various simple sugars on the time taken for the color to revert back to the pale yellow. (Food blue No. 2 was used as the dye.) It should be noted that the reaction of oxygen from the air to convert the colorless (or pale yellow) soap into a colored liquid during handwashing is very rapid. Thus, to study the reducing power of the various sugars the soap/dye solutions were shaken and the time taken to revert to colorless/pale yellow determined. The results are shown below:

| Sugar | Time (Seconds) |
|---|---|
| Glucose | 100 |
| Xylose | 80 |
| Galactose | 120 |
| Sucrose | No change |

As will be appreciated by those skilled in the art, changes and variations to the invention are considered to be within the ability of those skilled in the art. Examples of such changes are contained in the patents identified above, each of which is incorporated herein by reference in its entirety to the extent it is consistent with this specification. Such changes and variations are intended by the inventors to be within the scope of the invention.

What is claimed is:

1. A liquid cleansing formulation comprising:

a base material, the base material comprising water and a surfactant;

a reducing agent, wherein the reducing agent includes a sugar; and a redox dye, wherein the ratio of the reducing agent to the redox dye is at least about 5 to 1 and wherein the redox dye is present in the cleansing formulation in an amount of from about 0.001 to about 0.5 weight percent and the reducing agent is present in the cleansing formulation in an amount of from about 0.1 to about 2.0 weight percent;

wherein exposure of the liquid cleansing formulation to an excess concentration of oxygen causes oxidation of the redox dye and produces an observable color change.

2. The liquid cleansing formulation of claim 1, wherein the ratio of the reducing agent to the redox dye is at least about 10 to 1.

3. The liquid cleansing formulation of claim 1, wherein the sugar includes glucose, fructose, galactose, xylose, or combinations thereof.

4. The liquid cleansing formulation of claim 3, wherein the sugar includes glucose.

5. The liquid cleansing formulation of claim 1, wherein the reducing agent is present in the cleansing formulation in an amount of from about 0.3 to about 1.0 weight percent.

6. The liquid cleansing formulation of claim 1, wherein the redox dye includes Food Blue 1, Food Blue 2, Food Green 3, Basic Blue 17, resazurin, FD&C Blue No. 2, FD&C Green No. 3, 1,9-dimethyl methylene blue, saframine O, or combinations thereof.

7. The liquid cleansing formulation of claim 1, further comprising a pH sensitive dye.

8. The liquid cleansing formulation of claim 7, wherein the pH sensitive dye includes carminic acid, bromocresol green, chrysoidin, methyl red/Na salt, cochineal, chlorphenol red, bromocresol purple, 4-nitrophenol, alizarin, nitrazine yellow, bromothymol blue, brilliant yellow, neutral red, rosolic acid, phenol red, 3-nitrophenol, orange II, or combinations thereof.

9. The liquid cleansing formulation of claim 1, wherein the redox dye is present in the cleansing formulation in an amount of from about 0.003 to about 0.1 weight percent.

10. The liquid cleansing formulation of claim 1, further comprising a catalyst.

11. The liquid cleansing formulation of claim 10, wherein the catalyst is an enzyme.

12. The liquid cleansing formulation of claim 11, wherein the enzyme is glucose oxidase.

13. The liquid cleansing formulation of claim 1, further comprising a pH buffer.

14. The liquid cleansing formulation of claim 1, wherein the reducing agent further includes a hydroquinone, ascorbic acid, cysteine, dithionite, ferric ions, copper ions, silver ions, chlorine, phenol, permanganate ions, glucothione, iodine, iron protoporyphyrin complex, iron-sulfur protein, or combinations thereof.

15. The liquid cleansing formulation of claim 1, wherein the base material comprises an oil, emulsifier, film former, wax, perfume, preservative, emollient, solvent, thickener, humectant, chelating agent, stabilizer, pH adjuster, or combinations thereof.

16. The liquid cleansing formulation of claim 1, wherein the reducing agent has a reduction potential of about +0.9 to about −0.9 volts.

17. The liquid cleansing formulation of claim 1, wherein the formulation is a soap.

18. The liquid cleansing formulation of claim 1, wherein the formulation is a skin lotion.

19. The liquid cleansing formulation of claim 1, wherein the formulation is a hard surface cleaner.

* * * * *